United States Patent
Rossen et al.

(10) Patent No.: US 8,245,709 B2
(45) Date of Patent: Aug. 21, 2012

(54) RESPIRATION HUMIDIFIER

(75) Inventors: Thomas Rossen, Lübeck (DE); Jochim Koch, Ratzeburg (DE); Klaus Radomski, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1006 days.

(21) Appl. No.: 12/194,873

(22) Filed: Aug. 20, 2008

(65) Prior Publication Data

US 2009/0050150 A1 Feb. 26, 2009

(30) Foreign Application Priority Data

Aug. 21, 2007 (DE) .......................... 10 2007 039 391

(51) Int. Cl.
*F23D 11/00* (2006.01)
*F23D 14/00* (2006.01)

(52) U.S. Cl. ......... 128/203.26; 128/200.24; 128/203.12; 128/203.16; 128/203.27

(58) Field of Classification Search ............. 128/200.24, 128/203.12, 203.16, 203.17, 203.26, 203.27; 236/44 R
See application file for complete search history.

(56) References Cited

U.S. PATENT DOCUMENTS

| | | | |
|---|---|---|---|
| 6,435,180 B1 * | 8/2002 | Hewson et al. | 128/204.18 |
| 2004/0074493 A1 * | 4/2004 | Seakins et al. | 128/203.16 |
| 2006/0118113 A1 | 6/2006 | Bremner et al. | |

* cited by examiner

*Primary Examiner* — Lynne Anderson
*Assistant Examiner* — Bradley Philips
(74) *Attorney, Agent, or Firm* — McGlew and Tuttle, P.C.

(57) ABSTRACT

A respiration humidifier with a base unit (2), at least one sensor (3), which is connected to the base unit (2), and a mixing chamber (4), which is designed as a mixing chamber detachable from the base unit (2), with a gas-carrying area (5), wherein the mixing chamber (4) has at least one opening (6), through which the at least one sensor (3) is in connection with the gas-carrying area (5).

22 Claims, 5 Drawing Sheets

RESPIRATION HUMIDIFIER

CROSS REFERENCE TO RELATED APPLICATIONS

This application claims the benefit of priority under 35 U.S.C. §119 of German Patent Application 10 2007 039 391.3 filed Aug. 21, 2007, the entire contents of which are incorporated herein by reference.

FIELD OF THE INVENTION

The present invention pertains to a respiration/ventilation humidifier having a base unit with at least one sensor, and a mixing chamber detachable from the base unit. The mixing chamber has at least one said opening through which the sensor is in connection with a gas-carrying area of the mixing chamber.

BACKGROUND OF THE INVENTION

Respiration humidifiers for humidifying breathing gas for patients to be artificially respirated or ventilated are known from practice. They usually have a mixing chamber, in which a gas flowing in is enriched with moisture. Parameters of the breathing gas are detected by sensors in modern respiration humidifiers for controlling the humidifier.

An arrangement of a temperature sensor and of a flow sensor, in which the sensors are arranged in a piece of flexible breathing tube between the mixing chamber and a Y-piece of a flexible breathing tube system, is known from US 2006/0118 113 A1, and is incorporated by reference. These sensors are positioned in the flexible breathing tube system in sleeves provided especially for this purpose. The drawback of this arrangement is that the sensors must be introduced by the user into the flexible tube system and connected in a pneumatically sealed manner. There is a risk of leakage at the flexible breathing tube system. In addition, the clinical staff must establish an electric connection to the respiration humidifier. This requires an additional operation in making available the respiration humidifier for a new patient.

SUMMARY OF THE INVENTION

A primary object of the present invention is to provide a respiration humidifier which overcomes the drawbacks described in the state of the art shown. In particular, the respiration humidifier is optimized in clinical practice in terms of handling.

The object according to the present invention is accomplished by a respiration humidifier with a base unit controlling water vapor generation in the mixing chamber. A sensor is connected to the base unit and extends away from the base unit. The mixing chamber is repetitively attachable to, and detachable from, the base unit. The mixing chamber defines an opening for receiving the sensor. The opening, the sensor, the base unit and the mixing chamber are arranged to place the sensor through the hole and in communication with the gas-carrying area as the mixing chamber is attached to the base unit.

Thus, a respiration humidifier for enriching a breathing gas with moisture, which has at least one base unit, at least one sensor and a mixing chamber, which is detachable from the base unit and has a gas-carrying area, is provided according to the present invention, wherein the sensor is connected to the base unit and the mixing chamber has at least one opening, through which the at least one sensor is in connection with the gas-carrying area.

The mixing chamber has a breathing gas inflow channel and a breathing gas outflow channel. A breathing gas flowing in through the breathing gas inflow channel is enriched with moisture in the mixing chamber. The sensors used to control, regulate or monitor the respiration humidifier are advantageously provided essentially in an area in which enrichment of the gas flowing in with water vapor takes place. The sensors are electrically and mechanically connected to the base unit. Thus, the sensors advantageously remain rigidly connected to the base unit in case of a change of the mixing chamber and optionally of the flexible breathing tubes connected to the mixing chamber for preparation or replacement. One advantage is, moreover, that the mixing chamber can be manufactured at a low cost with or without flexible breathing tubes without integration of the sensors and a design as a disposable article becomes possible. In addition, an operation for connecting the sensors to the base unit is advantageously eliminated.

In a preferred embodiment of the present invention, the respiration humidifier has a mounting element, which protrudes at least partly into the mixing chamber and at which the at least one sensor is arranged. The sensor, which comes into contact with the breathing gas, is thus directly accessible for cleaning by the user after removal of the mixing chamber from the base unit. The at least one sensor can thus advantageously be subjected to disinfection by wiping in a convenient manner.

The provision of at least one channel within the mounting element for supplying water vapor into the mixing chamber in another preferred embodiment of the respiration humidifier according to the present invention facilitates the introduction of water vapor into the mixing chamber. To protect the sensor from moisture, the at least one sensor is surrounded at least partly with a breathable membrane or a film material. A sensor designed as a temperature sensor for regulating a moisture-generating unit is advantageously arranged at the breathing gas inflow channel of the mixing chamber.

In another embodiment, the respiration humidifier according to the present invention has another temperature sensor, which is arranged in the breathing gas outflow channel. The temperature of the breathing gas can be checked in this manner and overheating can be avoided. To avoid the effect of heat generated by the base unit, a reference sensor is provided within the base unit.

In yet another preferred embodiment, the respiration humidifier according to the present invention has a moisture sensor, which is provided with a controllable heater and is designed, preferably together with a flow sensor, as a common assembly unit. As a result, heat generated by a hot wire to prevent water of condensation on the flow sensor can advantageously continue to be used further for the moisture sensor. In another embodiment, the mixing chamber can be designed to receive water and thus be part of a moisture-generating unit.

Exemplary embodiments of the present invention are described in FIGS. 1 through 6. The variants of the respiration humidifier according to the present invention shown in FIGS. 1 through 6 may also be designed as a combination and do not represent a limitation of the scope of protection.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings, the present invention will be explained in detail with reference to the drawings attached, in which identical reference numbers designate identical structures.

Figure 1:
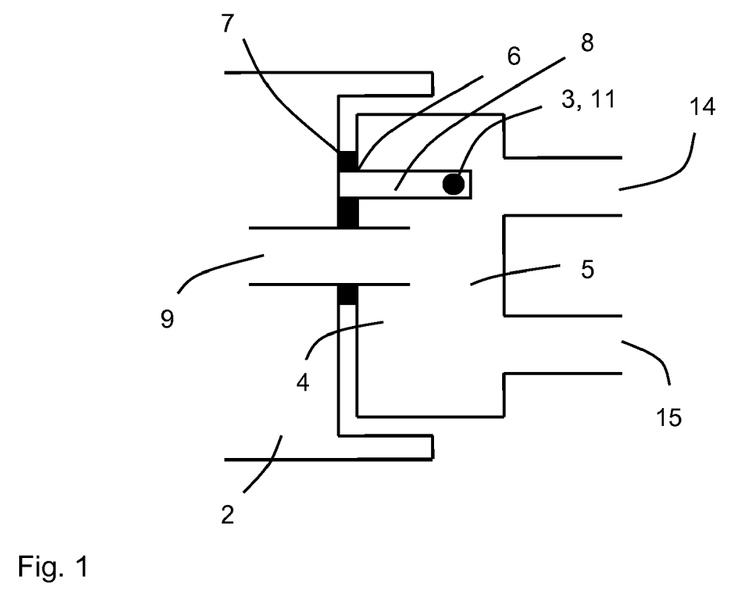
FIG. 1 is a schematic vertical sectional view of the device according to the present invention with a mounting element.

FIG. 1 shows a schematically simplified view of a mixing chamber 4 for humidifying a breathing gas to be humidified for the artificial respiration of a patient. The mixing chamber 4 has a gas-carrying area 5, a breathing gas inflow channel 14 and a breathing gas outflow channel 15, wherein a breathing gas to be humidified is fed through the breathing gas inflow channel 14 to the mixing chamber and leaves as humidified breathing gas after taking up moisture or water vapor through the breathing gas outflow channel 15 of the mixing chamber 4. In the state in which it is able to function, the mixing chamber 4 is connected to a base unit 2. The mixing chamber 4 has an opening 6 on a side facing the base unit 2. The opening 6 of the mixing chamber 4 has a sealing element 7 for sealing the gas-carrying area 5 of the mixing chamber 4 against the environment. A breathing gas entering through the breathing gas inflow channel 14 thus cannot escape from the mixing chamber 4. A mounting element 8 protrudes into the mixing chamber 4 through the opening 6 and is used to receive and fasten a sensor 3. The sensor 3 provided at the end of the mounting element 8 is designed as a temperature sensor 11. The temperature sensor 11 is rigidly connected to the base unit 2 via the mounting element 8. Furthermore, a channel 9 for supplying moisture in the form of water vapor into the mixing chamber 4 is provided in the mixing chamber 4. A breathing gas flowing in through the breathing gas inflow channel 14 can thus be enriched with a water vapor being discharged from the channel 9.

In another embodiment, the mounting element 8 has means for centering the mixing chamber 4 at the base unit 2 (not shown). In addition to or instead of the channel 9, a channel for supplying moisture into the mixing chamber 4 may be provided (not shown) in the mounting element 8. The temperature sensor 11 measures the temperature in the gas-carrying area 5, and a unit generating moisture, which unit is not shown, is controlled on the basis of the measured temperature values. The mixing chamber 4 can also be fastened by means of holding elements arranged at the base unit 2 and on an outside of the mixing chamber 4. For example, the base unit 2 may thus have a conical holding element, which is caused to mesh an eyelet-shaped holding element arranged on the outer side of the mixing chamber 4 at the time of fastening the mixing chamber 4 to the base unit 2. The temperature sensor 11 is arranged directly on the outer side of the base unit 2 in this embodiment, not shown, and is in connection through the opening 6 of the mixing chamber 4 with the gas-carrying area 5 of the mixing chamber 4.

Figure 2:
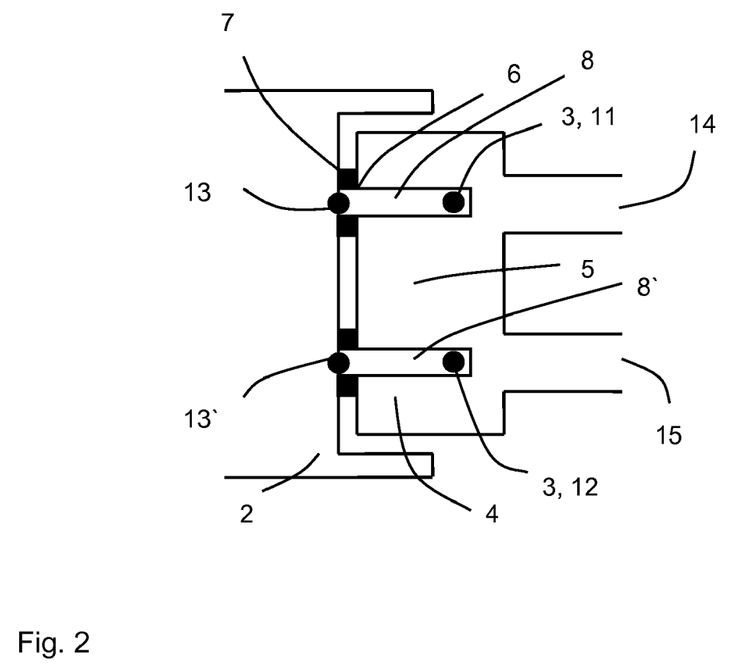
FIG. 2 is a schematic vertical sectional view of the device according to the present invention with two mounting elements.

FIG. 2 shows an advantageous embodiment of the device according to the present invention with two mounting elements 8 and 8', which are provided for receiving and fixing at least one respective sensor 3 each. The at least one sensor 3 is designed as a temperature sensor 11 and is provided on a side of the first mounting element 8, which side faces away from the base unit 2. The temperature sensor 11 is arranged in the vicinity of the breathing gas inflow channel 14 in order to measure a temperature of the breathing gas to be humidified, which is flowing into the mixing chamber 4. In the embodiment according to FIG. 2, an additional sensor 3 is provided, which is designed as a second temperature sensor 12. The temperature sensor 12 is provided on a side of a second mounting element 8', which side faces away from the base unit 2. The temperature sensor 12 is arranged in the vicinity of the breathing gas outflow channel 15 in order to measure a temperature of the breathing gas, which is mixed with moisture and is flowing through the breathing gas outflow channel 15 of the mixing chamber 4.

The temperature values determined by the temperature sensor 11 can be advantageously used to regulate a moisture-generating unit. The breathing gas enriched with moisture can be heated. Protection against overheating of the breathing gas enriched with moisture is ensured by an analysis of the values determined by the temperature sensor 12. Both the temperature sensor 11 and the temperature sensor 12 are mechanically rigidly connected to the base unit 2 via the respective mounting element 8 and 8'. In another embodiment, the mounting element 8 and/or 8' may have means for centering the mixing chamber 4 on the base unit 2 (not shown). The mounting element 8 and/or 8' may, furthermore, be equipped in an advantageous manner with means for fixing the mixing chamber 4 to the base unit 2 (not shown).

A respective additional temperature sensor each, which is connected as a reference temperature sensor 13 and 13' for the temperature sensors 11 and 12, is arranged on the base unit 2 preferably in the area of the base of the mounting elements 8 and 8'. Due to the rigid connection of the temperature sensors 11 and 12 to the base unit 2, a heat flux may develop from the base unit 2 to the temperature sensors 11 and 12, and the measurement of the temperatures being measured in the gas-carrying area 5 may be influenced by the heat flux. This is especially critical when the temperature of the base unit 2 is markedly higher than the temperatures of the gas-carrying area 5 of the mixing chamber 4. The respective temperature detected by the temperature sensors 11 and 12 can be corrected with the temperatures detected by the reference temperature sensors 13 and 13'.

Figure 3:
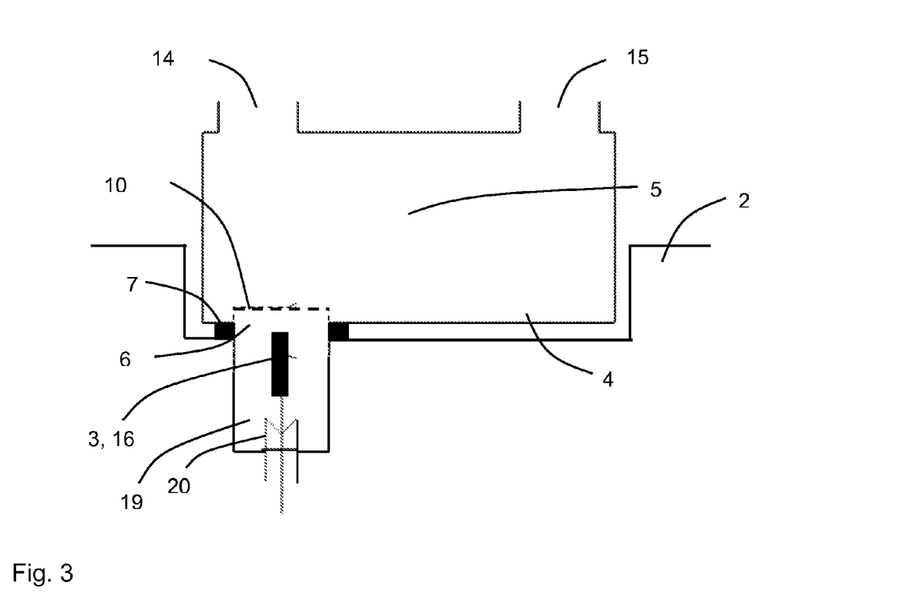
FIG. 3 is a schematic vertical sectional view of the device according to the present invention with a sensor element arranged recessed in the base unit.

In another embodiment of the respiration humidifier according to the present invention, FIG. 3 shows a sensor 3 arranged in a measuring chamber 19 arranged recessed in the base unit 2. The sensor 3 is designed as a moisture sensor 16 for measuring the moisture content in the gas-carrying area 5, especially in the breathing gas inflow channel 14 of the mixing chamber 4. The moisture sensor 16 is in connection with breathing gas of the gas-carrying area 5 through the opening 6 of the mixing chamber 4. On the surface of the base unit 2, the measuring chamber 19 preferably has a circumferential collar, which passes through the opening 6 into the mixing chamber 4. The opening 6 of the mixing chamber 4 is sealed by the sealing element 7, so that no breathing gas of the gas-carrying area 5 can escape into the environment. The moisture sensor 16 is preferably separated from the gas-carrying area 5 of the mixing chamber 4 by a breathable membrane 10. The breathable membrane 10 has a hydrophobic surface, which is permeable to gases but impermeable to liquids. The moisture sensor 16 is thus protected from the direct action of liquids. To avoid condensation from forming, the moisture sensor 16 may be heated by a heater 20 in the measuring chamber 19. However, it is also possible to introduce heat from the outside into the measuring chamber 19. The heat may be generated by means of a separate heater or by the waste heat of users of the base unit 2 (not shown). A temperature sensor 11 may be provided for the moisture sensor 16 on the breathing gas inflow channel 14 and a temperature sensor 12 may be provided on the breathing gas outflow channel 15. Another reference temperature sensor 13, not shown, may be provided in the base unit 2.

Figure 4:
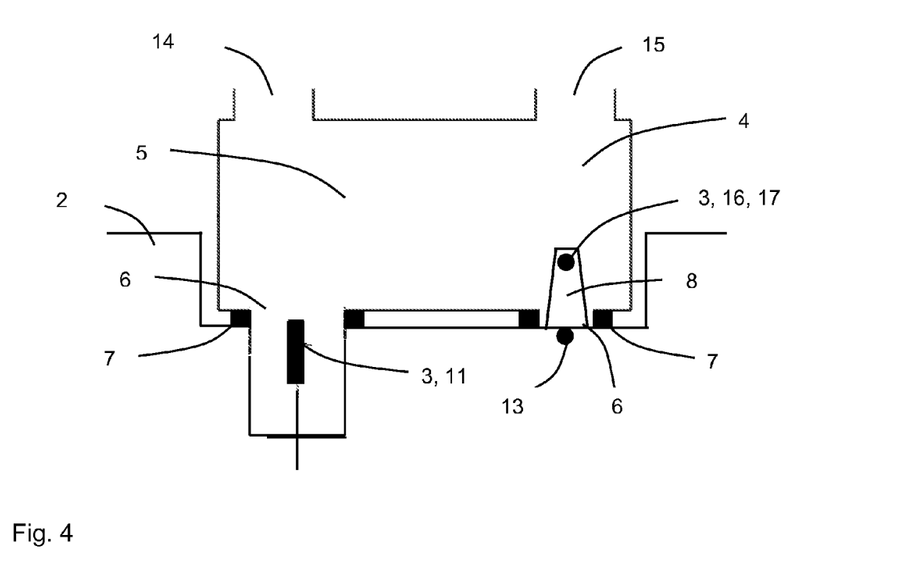
FIG. 4 is a schematic vertical sectional view of another embodiment of the device according to the present invention.

In the embodiment of the respiration humidifier according to the present invention shown in FIG. 4, the at least one sensor 3 is in connection with the gas-carrying area 5 in, or adjacent, the breathing gas inflow channel 14. The at least one sensor 3 is designed as a temperature sensor 11 and detects the temperature of the breathing gas flowing in the breathing gas inflow channel 14 for regulating a unit generating moisture, not shown. The temperature sensor 11 preferably protrudes into the gas-carrying area 5 of the breathing gas inflow channel 14 through the opening 6 of the mixing chamber 4, but it may also be arranged, as in the exemplary embodiment according to FIG. 3, in a measuring chamber 19 of the base unit 2, which measuring chamber is arranged in a recessed manner. The opening 6 of the mixing chamber 4 is in turn provided with a sealing element 7 for sealing the gas-carrying area 5 against the environment. Two other sensors 3 are located on the mounting element 8, which protrudes through the opening 6 into the mixing chamber 4. These are a moisture sensor 16 and a flow sensor 17, which are preferably designed together as one assembly unit. Due to the design as one common assembly unit, a heat generated by a heating wire to avoid water of condensation from forming at the flow sensor 17 can be used, furthermore, to prevent water of condensation from forming at the moisture sensor 16. The moisture sensor 16 and the flow sensor 17 are mechanically and electrically connected to the base unit 2. An electrical connection to the base unit 2 is provided in an advantageous manner within the mounting element 8. The mounting element 8 may advantageously have a channel for supplying water vapor for enriching the gas-carrying area 5 with moisture (not shown). A temperature sensor 12 (not shown) may in turn be provided in the area of the breathing gas outflow channel 15 of the mixing chamber 4. At least one reference temperature sensor 13 is arranged in the area of the base unit 2.

Figure 5:
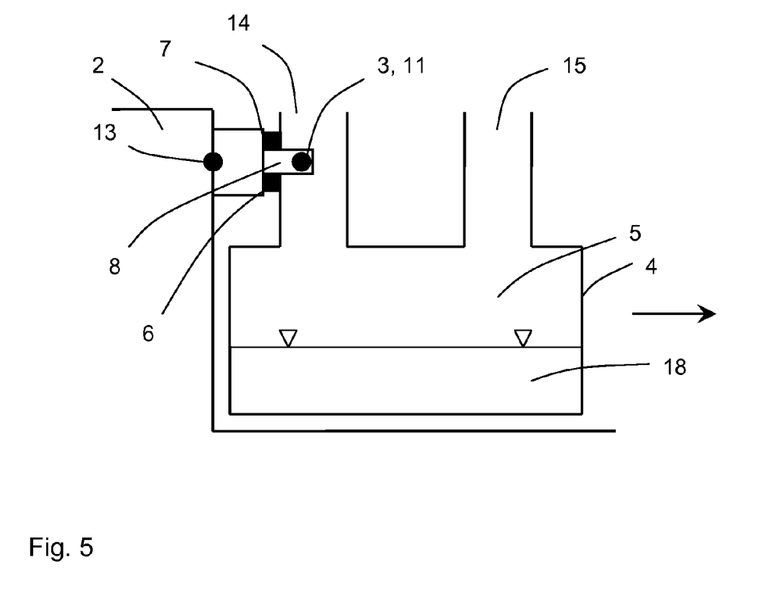
FIG. 5 is a schematic vertical sectional view of the device according to the present invention with a mixing chamber designed to receive water.

FIG. 5 shows an embodiment of the respiration humidifier according to the present invention with a mixing chamber 4, which is designed to receive water 18. A water vapor to enrich the gas-carrying area 5 is not introduced into the mixing chamber 4, but it is rather formed within the mixing chamber 4. Water 18, which is heated to evaporate by a heat source, especially by a hot plate (not shown) provided in the base unit 2, is stored in the mixing chamber 4. The mixing chamber 4 is removed from the base unit 2 for replacement corresponding to the direction of the arrow shown. A mounting element 8, which is formed on the base unit 2, has a temperature sensor 11 at its ends and which protrudes through the opening 6 into the mixing chamber 4, especially into the breathing gas inflow channel 14, is provided in the area of the breathing gas inflow channel 14 of the mixing chamber 4. A reference temperature sensor 13 is arranged on the base unit 2 in the area of the base of the mounting element 8. Another temperature sensor 12 (not shown) may be provided in the breathing gas outflow channel 15. In another embodiment of the device according to the present invention (not shown), the temperature sensor 12 may be provided in the breathing gas outflow channel 15 also without the temperature sensor 11 in the breathing gas inflow channel 14. Additional sensors 3 may be provided as moisture sensors 16 and/or flow sensors 17 on the base unit 2, and be in connection in the manner according to the present invention with the gas-carrying area 5 of the mixing chamber 4 through the opening 6 (not shown). The moisture sensor 16 and the flow sensor 17 are designed here as a common assembly unit in a preferred embodiment.

Figure 6:
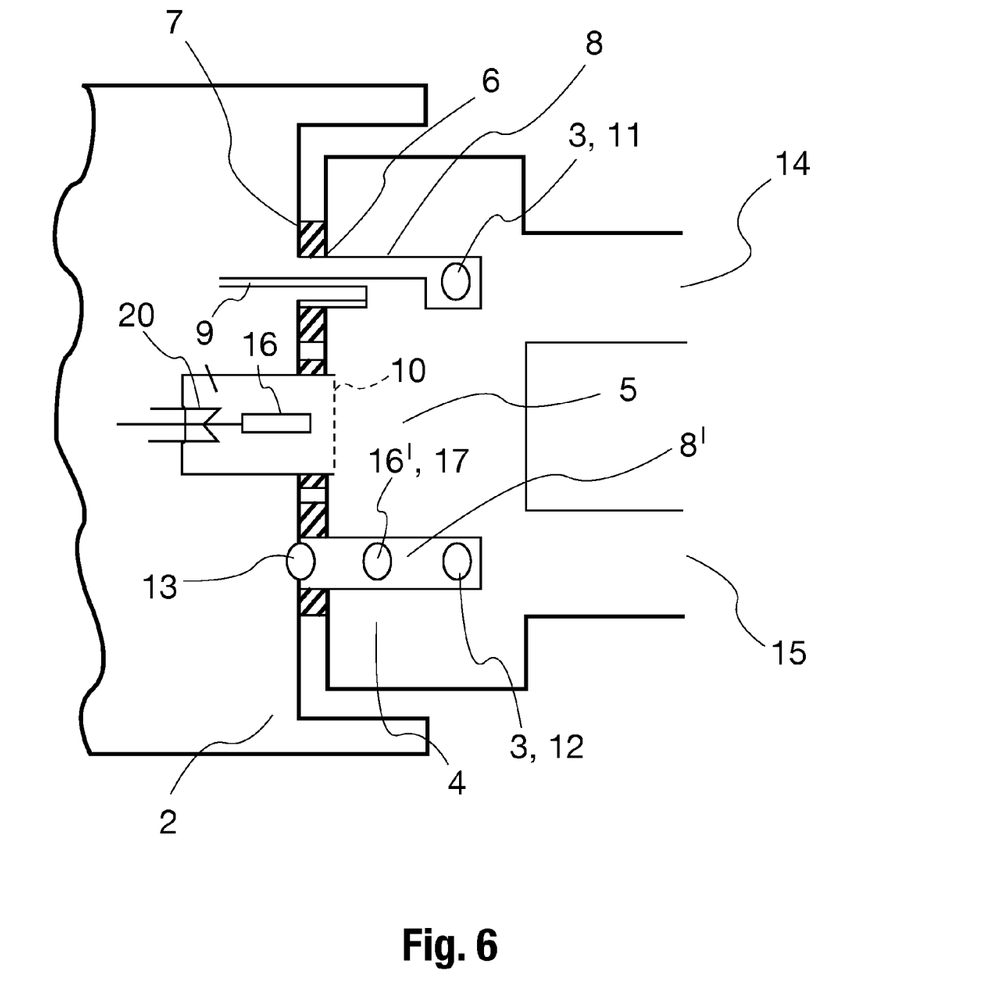
FIG. 6 is a schematic vertical sectional view of another embodiment of the device according to the present invention.

FIG. 6 shows an embodiment with a plurality of sensors 3 and where the mounting element 8 is provided on the base unit 2 for extending at least one of the sensors 3 away from the base unit 2 and the channel 9 is formed within the mounting element 8. The sensors 3 include a moisture sensor 16 surrounded at least partly with a breathable membrane 10. The moisture sensor 16 is provided with a controllable heater 20. Alternatively a moisture sensor 16' can be combined with a flow sensor 17 and designed as one assembly unit. The mixing chamber has a breathing gas inflow channel 14 and a breathing gas outflow channel 15 with a first temperature sensor 11 arranged in the breathing gas inflow channel 14, and a second temperature sensor 12 arranged in the breathing gas outflow channel 15. A reference temperature sensor 13 is provided in the base unit 2.

Figure 7:
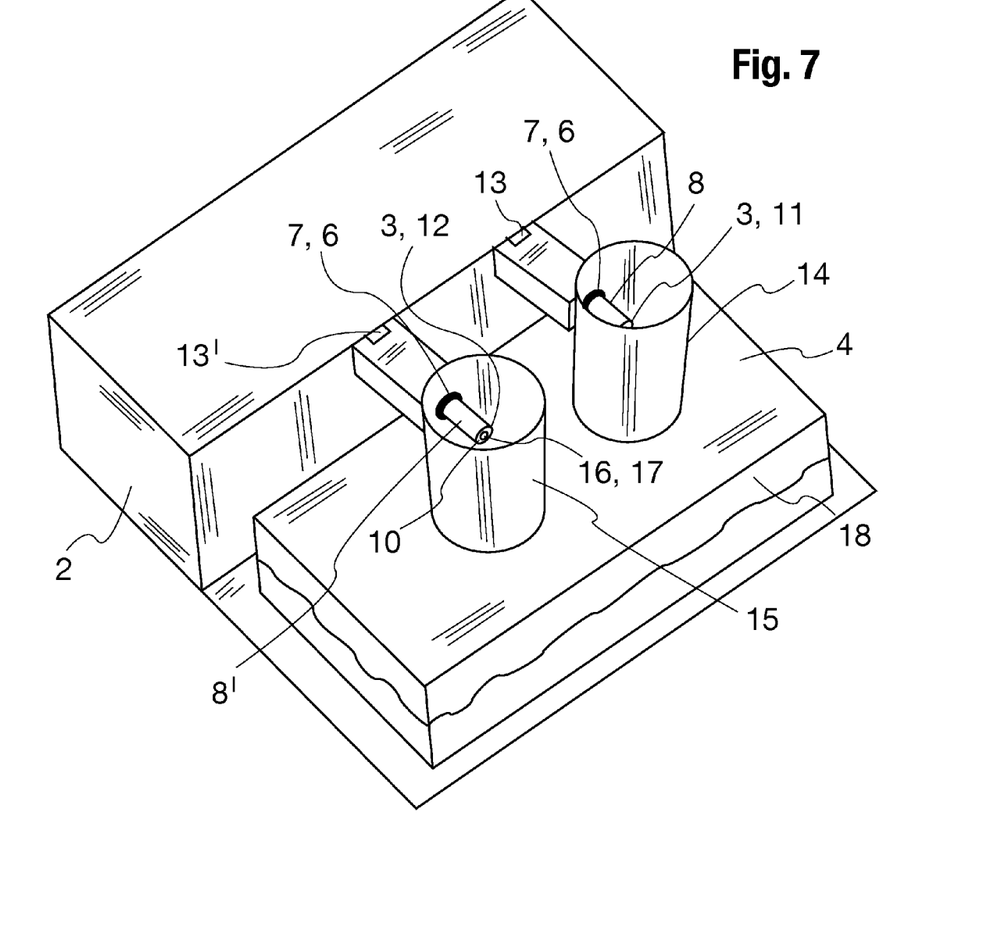
FIG. 7 is a view of another embodiment of the device according to the present invention embodiment having many of the features of the embodiments of FIGS. 2 and 5.

FIG. 7 is embodiment having many of the features of the embodiments of FIGS. 2 and 5. The mixing chamber 4 is arranged on the base unit 2, and the mixing chamber 4 is arranged to hold water 18 which is heated by the base unit 2. The mixing chamber 4 slides onto the base unit 2 and the mounting elements 8, 8' through the openings 6 with the sealing elements 7. The mounting elements 8, 8' include sensors, such as temperature sensors 11, 12, moisture sensor 16 and flow sensor 17. A breathable membrane 10 can surround the moisture sensor 16, and a heater 20 (not shown) can be provided as in FIG. 3. Temperature sensors 13 and 13' can be mounted on the base unit 2 to correct the temperature sensors 11 and 12 as in FIG. 2.

While specific embodiments of the invention have been shown and described in detail to illustrate the application of the principles of the invention, it will be understood that the invention may be embodied otherwise without departing from such principles.

LIST OF REFERENCE NUMBERS

1 Base unit
3 Sensor
4 Mixing chamber
5 Gas-carrying area
6 Opening
7 Sealing element
8, 8' Mounting element
9 Channel for supplying water vapor
10 Breathable membrane
11 Temperature sensor
12 Temperature sensor
13, 13' Reference temperature sensor 14 Breathing gas inflow channel
15 Breathing gas outflow channel
16 Moisture sensor
17 Flow sensor
18 Water
19 Measuring chamber
20 Heater

What is claimed is:

1. A respiration humidifier comprising:
a base unit;
a sensor connected to said base unit;
a mixing chamber detachable from said base unit and including a gas-carrying area with an inflow opening for receiving breathing gas and with an outflow opening for delivering the breathing gas mixed with the water vapor, said mixing chamber having a wall defining a sensor connection opening through which said sensor is in connection with said gas-carrying area; and
a mounting element supporting said sensor relative to said base unit for extending said sensor away from said base unit and positioning said sensor in communication with said gas-carrying area via said sensor connection opening, upon said mixing chamber being attached to said base unit.

2. A respiration humidifier in accordance with claim 1, further comprising a sealing element for sealing said mounting element at said wall defining said sensor connection opening wherein said sealing element seals said gas-carrying area of said mixing chamber against a surrounding environment.

3. A respiration humidifier in accordance with claim 1, wherein said mounting element protrudes into said mixing chamber as said mixing chamber is attached to said base unit.

4. A respiration humidifier in accordance with claim 3, wherein said mounting element has means for mounting said mixing chamber onto said base unit.

5. A respiration humidifier in accordance claim 1, wherein said mixing chamber has a channel for supplying water vapor from said base unit into said gas-carrying area of said mixing chamber.

6. A respiration humidifier in accordance with claim 5, wherein said mounting element is provided on said base unit for extending said sensor away from said base unit and said channel is formed within said mounting element.

7. A respiration humidifier in accordance with claim 1, wherein said sensor is surrounded at least partly with a breathable membrane.

8. A respiration humidifier in accordance with claim 1, wherein said mixing chamber has a breathing gas inflow channel and a breathing gas outflow channel.

9. A respiration humidifier in accordance with claim 1, wherein said sensor comprises a temperature sensor.

10. A respiration humidifier in accordance with claim 8, wherein said sensor is a temperature sensor and is arranged in said breathing gas inflow channel.

11. A respiration humidifier in accordance with claim 8, wherein said sensor is a temperature sensor and is arranged in said breathing gas outflow channel.

12. A respiration humidifier in accordance with claim 9, wherein a reference temperature sensor is provided in said base unit.

13. A respiration humidifier in accordance with claim 1, wherein said sensor is designed as a moisture sensor.

14. A respiration humidifier in accordance with claim 13, wherein said moisture sensor is provided with a controllable heater.

15. A respiration humidifier in accordance with claim 1, wherein said sensor is designed as a flow sensor.

16. A respiration humidifier in accordance with claim 1, wherein said sensor includes a flow sensor and a moisture sensor designed as one assembly unit.

17. A respiration humidifier in accordance with claim 1, wherein mixing chamber is designed to receive water.

18. A respiration humidifier in accordance with claim 4, wherein said opening has a sealing element for sealing said gas-carrying area of said mixing chamber against a surrounding environment;
said mixing chamber has a channel for supplying water vapor from said base unit into said gas-carrying area of said mixing chamber;
a mounting element is provided on said base unit for extending said sensor away from said base unit, said channel is formed within said mounting element;
said sensor is surrounded at least partly with a breathable membrane;
said mixing chamber has a breathing gas inflow channel and a breathing gas outflow channel;
said sensor includes a first temperature sensor arranged in said breathing gas inflow channel;
said sensor includes a second temperature sensor arranged in said breathing gas outflow channel;
a reference temperature sensor is provided in said base unit;
said sensor includes a moisture sensor provided with a controllable heater;
said sensor includes a flow sensor designed as one assembly unit with a moisture sensor.

19. A respiration humidifier comprising:
a base unit controlling water vapor generation;
a sensor mount fixed to said base unit;
a sensor connected to said base unit and supported by said senor mount extending away from said base unit; and
a mixing chamber arranged attachable to, and detachable from, said base unit, said mixing chamber enclosing a gas-carrying area with an inflow opening for receiving breathing gas and with an outflow opening for delivering the breathing gas mixed with the water vapor, said mixing chamber defining a sensor opening receiving said sensor and a portion of said sensor mount such that said portion of said sensor mount extends trough said sensor opening toward said mixing chamber and positions said sensor in said mixing chamber in communication with said gas-carrying area with said mixing chamber attached to said base unit, said opening, said sensor mount, said sensor, said base unit and said mixing chamber being arranged to place said sensor through said opening and in communication with said gas-carrying area as said mixing chamber is attached to said base unit.

20. A respiration humidifier in accordance with claim 19, further comprising a sealing element for sealing around said mounting element at said wall defining said opening to seal said gas-carrying area of said mixing chamber, at said opening, against a surrounding environment.

21. A respiration humidifier in accordance with claim 20, wherein mixing chamber comprises a water reservoir for providing water in communication with said gas-carrying area.

22. A respiration humidifier comprising:
a base unit with a heat source for controlling water vapor generation;
a mixing chamber attachable to, and detachable from said base unit, said mixing chamber having a wall enclosing a gas-carrying area with an inflow area having an inflow opening for receiving breathing gas into said gas-carrying area and with an outflow area having an outflow opening for delivering the breathing gas mixed with the water vapor out of said gas-carrying area and said wall enclosing a water reservoir area with water in fluid communication with said gas-carrying area, the water being heated by said heat source of said base unit with said mixing chamber attached to said base unit, said wall defining a sensor opening;

a sensor; and a sensor mount fixed to said base unit and supporting said sensor relative to said base unit for extending said sensor away from said base unit, a portion of said sensor mount extending through said sensor opening into said mixing chamber with said mixing chamber attached to said base unit and positioning said sensor in communication with said gas-carrying area and in or adjacent to at least one of said inflow area and said outflow area.

* * * * *